US009365826B2

(12) United States Patent
Meyer et al.

(10) Patent No.: US 9,365,826 B2
(45) Date of Patent: Jun. 14, 2016

(54) CARDIOMYOCYTE MEDIUM WITH DIALYZED SERUM

(75) Inventors: Nathan Meyer, Mazomanie, WI (US); Brad Swanson, Waunakee, WI (US); Steve Fiene, Middleton, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 1290 days.

(21) Appl. No.: 13/164,461

(22) Filed: Jun. 20, 2011

(65) Prior Publication Data

US 2011/0312090 A1    Dec. 22, 2011

Related U.S. Application Data

(60) Provisional application No. 61/356,136, filed on Jun. 18, 2010, provisional application No. 61/356,916, filed on Jun. 21, 2010.

(51) Int. Cl.
*C12N 5/077* (2010.01)

(52) U.S. Cl.
CPC .......... *C12N 5/0657* (2013.01); *C12N 2500/00* (2013.01); *C12N 2501/999* (2013.01)

(58) Field of Classification Search
CPC ............. C12N 5/0657; C12N 2506/45; C12N 2510/00; C12N 2830/008; C12N 2501/999
USPC .................... 435/325, 366, 374, 14
See application file for complete search history.

(56) References Cited

U.S. PATENT DOCUMENTS

| | | | |
|---|---|---|---|
| 5,843,780 A | 12/1998 | Thomson | 435/363 |
| 6,200,806 B1 | 3/2001 | Thomson | 435/366 |
| 6,602,711 B1 | 8/2003 | Thomson et al. | 435/378 |
| 7,029,913 B2 | 4/2006 | Thomson | 435/363 |
| 7,781,214 B2 | 8/2010 | Smith et al. | 435/377 |
| 2006/0057124 A1 | 3/2006 | Shim et al. | |
| 2008/0038820 A1 | 2/2008 | Rudy-Reil | 435/377 |
| 2008/0226558 A1 | 9/2008 | Keller et al. | 724/9.1 |
| 2008/0254003 A1 | 10/2008 | Passier et al. | 424/93.7 |
| 2008/0254513 A1 | 10/2008 | Cayli | 435/70.1 |
| 2009/0047739 A1 | 2/2009 | Gold et al. | 435/377 |
| 2009/0275132 A1 | 11/2009 | Hattori et al. | |
| 2010/0003757 A1 | 1/2010 | Mack et al. | 435/455 |
| 2010/0233804 A1 | 9/2010 | Zhou et al. | 435/354 |
| 2011/0065103 A1 | 3/2011 | Sahin et al. | 435/6.16 |

FOREIGN PATENT DOCUMENTS

| | | |
|---|---|---|
| WO | WO 01/51616 | 7/2001 |
| WO | WO 03/004626 | 1/2003 |
| WO | WO 2007/088874 | 8/2007 |

OTHER PUBLICATIONS

Cheng et al. Cardiomyocyte-restricted peroxisome proliferatoractivated receptor-delta deletion perturbs myocardial fatty acid oxidation and leads to cardiomyopathy. Nature Medicine. 2004. vol. 10, No. 11, p. 1245-1250.*
Stanisz et al. Comparative Energy Metabolism in Cultured Heart Muscle and HeLa Cells. Journal of Cellular Physiology 115: 320-330 (1983).*
Wice et al. Serum Factors That Stimulate Fatty Acid Oxidation: Properties of Factors. Journal of Cellular Physiology 126:133-140 (1986).*
L-15 Medium Leibovitz. 2007. Sigma-Aldrich p. 1.*
Neonatal Cardiomyocyte Isolation System. Protocol page. dated Feb. 28, 2003 (http://web.archive.org/web/20030228203929/http://worthington-biochem.com/NCIS/default.html). p. 1-7.*
International Search Report and Written Opinion, issued in International Patent Application No. PCT/US2011/041103, mailed on Feb. 17, 2012.
Muller-Werdan et al., "Xenoreactive natural antibodies and induced antibodies—their effects on beating cardiomyocytes as a model of xenograft," *Molecular and Cellular Biochemistry*, 160/161:315-324, 1996.
Van Kesteren et aL, "Cultured neonatal rat cardiac myocytes and fibroblasts do not synthesize rennin or angiotensinogen: evidence for stretch-induced cardiomyocyte hypertrophy independent of angiotensin II," *Cardiovascular Research*, 43:148-156, 1999.
Schluter et al., "Parathyroid hormone induces protein kinase C but not adenylate cyclase in adult cardiomyocytes and regulates cyclic AMP levels via protein kinase C-dependent phosphodiesterase activity," *Biochemical Journal*, 310:439-444, 1995.
Bialik et al., "The mitochondrial apoptotic pathway is activated by serum and glucose deprivation in cardiac myocytes," *Circulation Research*, 85:403-414, 1999.
Extended European Search Report issued in European Application No. 11796584.8, mailed Nov. 15, 2013.
Office Action issued in Australian Application No. 2011268056, mailed Dec. 24, 2013.
Office Action issued in European Application No. 11796548.8, mailed Jul. 2, 2014.
PCT International Preliminary Report on Patentability issued in International Application No. PCT/US2011/041103, mailed Jan. 3, 2013.
Altamirano, et al., "Improvement of CHO cell culture medium formulation: simultaneous substitution of glucose and glutamine," *Biotechnol. Prog.*, 16:69-75, 2000.
Amit, et al., "Clonally derived human embryonic stem cell lines maintain pluripotency and proliferative potential for prolonged periods of culture," *Dev. Biol.*, 227:271-8, 2000.
Das, et al., "Long-term culture of embryonic rat cardiomyocytes on an organosilane surface in a serum-free medium," *Biomaterials*, 25:5643-7, 2004.
Klimanskaya, et al., "Human embryonic stem cells derived without feedwells," *Lancet*, 365:1636-41, 2005.
Li, et al., "Long-term survival of xenografted neonatal cardiomyocytes by adenovirus-mediated CTLA4-Ig expression and CD40 blockade," *Circulation*, 108:1760-5, 2003.

(Continued)

*Primary Examiner* — Taeyoon Kim
(74) *Attorney, Agent, or Firm* — Parker Highlander PLLC

(57) ABSTRACT

Methods and composition for maintenance of cardiomyocytes are provided. For example, in certain aspects methods including culturing the cardiomyocytes in a medium essentially free of serum or containing dialyzed serum to maintain long-term purity. In further aspects, methods for modulation of cardiomyocytes may be provided.

15 Claims, 5 Drawing Sheets

(56) References Cited

OTHER PUBLICATIONS

Marvin, et al., "Inhibition of Wnt activity induces heart formation from posterior mesoderm," *Genes Dev.*, 15:316-27, 2001.

Mesarić and Decker, "Labeling of precursor pools for glycosphingolipid biosynthesis. Incorporation of [3H]galactose by rat hepatocytes in primary culture," *Biol. Chem. Hoppe. Seyler.*, 371:1051-7, 1990.

Narazaki, et al., "Directed and systematic differentiation of cardio-vascular cells from mouse induced pluripotent stem cells," *Circulation*, 118:498-506, 2008.

Reubinoff, et al., "Embryonic stem cell lines from human blastocysts: somatic differentiation in vitro," *Nat. Biotechnol.*, 18:399-404, 2000.

Scalia, et al., "Regulation of the Akt/Glycogen synthase kinase-3 axis by insulin-like growth factor-II via activation of the human insulin receptor isoform-A," *J. Cell. Biochem.*, 82:610-8, 2001.

Schneider and Mercola, "Wnt antagonism initiates cardiogenesis in Xenopus laevis," *Genes Dev.*, 15:304-15, 2001.

Takahashi and Yamanaka, "Induction of pluripotent stem cells from mouse embryonic and adult fibroblast cultures by defined factors," *Cell*, 126:663-76, 2006.

Thomson and Marshall, "Primate embryonic stem cells," *Curr. Top Dev. Biol.*, 38:133-65, 1998.

Thomson and Odorico, "Human embryonic stem cell and embryonic germ cell lines," *Trends Biotechnol.*, 18:53-7, 2000.

Thomson, et al., "Isolation of a primate embryonic stem cell line," *Proc. Natl. Acad. Sci. USA*, 92:7844-8, 1995.

Tirumalai, et al., "Characterization of the low molecular weight human serum proteome," *Mol. Cell Proteomics*, 2:1096-103, 2003.

U.S. Appl. No. 12/478,154, entitled "Methods for the Production of IPS Cells Using Non-Viral Approach," filed Jun. 4, 2009.

U.S. Appl. No. 12/723,063, entitled "Generation of Pluripotent Stem Cells Using Recombinant Proteins," filed Mar. 12, 2010.

U.S. Appl. No. 12/735,060, entitled "Use of RNA for Reprogramming Somatic Cells," filed Nov. 24, 2010.

U.S. Appl. No. 61/184,546, entitled "Reprogramming T Cells," filed Jun. 5, 2009.

Volz, et al., "Longevity of adult ventricular rat heart muscle cells in serum-free primary culture," *J. Mol. Cell Cardiol.*, 23:161-72, 1991.

Wagner, et al., "Growth and metabolism of human tumor kidney cells on galactose and glucose," *Cytotechnology*, 7:7-13, 1991.

Xu, et al., "Feeder-free growth of undifferentiated human embryonic stem cells," *Nat. Biotechnol.*, 19:971-4, 2001.

Xu, et al., "Human embryonic stem cell-derived cardiomyocytes can be maintained in defined medium without serum," *Stem Cells Dev.*, 15:931-41, 2006.

Ying, et al., "BMP induction of Id proteins suppresses differentiation and sustains embryonic stem cell self-renewal in collaboration with STAT3," *Cell*, 115:281-92, 2003.

Yu and Thompson, "Pluripotent stem cell lines," *Genes Dev.*, 22:1987-97, 2008.

Yu, et al., "Development of a cell-based hepatitis C virus infection fluorescent resonance energy transfer assay for high-throughput antiviral compound screening," *Antimicrob. Agents Chemother.*, 53:4311-9, 2009.

Yu, et al., "Induced pluripotent stem cell lines derived from human somatic cells," *Science*, 318:1917-20, 2007.

Zajdel, et al., "A primary cell culture model for defective cardiac myofibrillogenesis in Mexican axolotl embryos," *In Vitro Cell Dev. Biol. Anim.*, 33:677-80, 1997.

Zandstra, et al., "Scalable production of embryonic stem cell-derived cardiomyocytes," *Tissue Eng.*, 9:767-78, 2003.

Zhang, et al., "Functional cardiomyocytes derived from human induced pluripotent stem cells," *Circ. Res.*, 104:e30-41, 2009.

Arstall, "Human ventricular myocytes in vitro exhibit both early and delayed preconditioning responses to stimulated ischemia," *Journal of Molecular and Cellular Cardiology*, 30(5):1019-1025, 1998.

Office Action issued in European Application No. 11796584.8, mailed Feb. 27, 2015.

Feinberg et al., "Functional Differences in Engineered Myocardium from Embryonic Stem Cell-Derived versus Neonatal Cardiomyocytes," *Stem Cell Reports*, 1:387-396, 2013.

Phanstiel et al., "Proteomic and phosphoproteomic comparison of human ES and iPS cells," *Nat Methods*, 8(10):821-827, 2012.

Müller et al. "Selection of ventricular-like cardiomyocytes from ES cells in vitro," *The FASEB Journal*, 14(15):2540-2548, 2000.

Office Action issued in Japanese Application No. 2013-515582, mailed Aug. 21, 2015, and English languagC45e translation thereof.

* cited by examiner

CARDIOMYOCYTE MEDIUM WITH DIALYZED SERUM

This application claims priority to U.S. Application No. 61/356,136 filed on Jun. 18, 2010 and U.S. Application No. 61/356,916 filed on Jun. 21, 2010, the entire disclosure of which are specifically incorporated herein by reference in its entirety without disclaimer.

BACKGROUND OF THE INVENTION

1. Field of the Invention

The present invention relates generally to the field of cell culture. More particularly, it concerns cardiomyocyte maintenance and modulation.

2. Description of Related Art

A central challenge for research in regenerative medicine is to develop cell compositions that can help reconstitute cardiac function. It is estimated that nearly one in five men and women have some form of cardiovascular disease (National Health and Nutrition Examination Survey lil, 1988-94, Center of Disease Control and the American Heart Association). Widespread conditions include coronary heart disease (5% of the population), congenital cardiovascular defects (0.5%), and congestive heart failure (3%). The pharmaceutical arts have produced small molecule drugs and biological compounds that can help limit the damage that occurs as a result of heart disease, but there is nothing commercially available to help regenerate the damaged tissue.

With the objective of developing a cell population capable of cardiac regeneration, research has been conducted on several different fronts, including the use of functional cardiomyocytes. A potential source of regenerative cells for treating cardiac disease is cardiomyocytes derived in vitro from pluripotent stem cells of various kinds, especially induced pluripotent stem cells. However, a number of obstacles have stood in the way of developing a paradigm for maintaining homogeneity of cardiomyocyte lineage cells in culture.

Commercialization of these technologies for use in in vitro drug screening assays and/or regenerative medicine will benefit from further improvement in the expansion and differentiation protocols to improve cell homogeneity and yield.

SUMMARY OF THE INVENTION

Aspects of the present invention overcome a major deficiency in the art by providing a method for maintaining the purity, particularly in terms of homogeneity, of cardiomyocyte populations. In certain embodiments, there is provided a method for maintaining the purity of a population of purified cardiomyocytes comprising: culturing a purified population of cardiomyocytes in a medium used described below, wherein the population is cultured for at least one week to seven months and maintains the purity of cardiomyocytes.

There may also be provided a method for modulating the electrical activity of cardiomyocytes, comprising: culturing a population of cardiomyocytes in a medium described below, wherein the beating rate of the cardiomyocyte culture has enhanced stability relative to a medium containing serum that has not been treated to remove low molecular weight molecules.

Such a medium may be essentially free of serum; or contains serum, wherein the serum or medium has been treated to remove low molecular weight molecules (including low molecular weight growth factors). For example, the serum or the medium may be essentially free of low molecular weight growth factors or essentially free of low molecular weight molecules. The low molecular weight molecules or growth factors may have a molecular weight of less than about 1, 2, 3, 4, 5, 6, 7, 8, 9, 10, 15, 20, 25, 30 kD or any intermediate size or size range. For example, the medium could contain dialyzed serum. Particularly, the serum could be dialyzed with a membrane with molecular weight cutoff of 1, 2, 3, 4, 5, 6, 7, 8, 9, 10, 15, 20, 25, 30 kD or any range derivable therefrom.

Certain aspects of the invention may also provide a composition comprising a cell population of cardiomyocytes and a medium. The medium may contain serum, wherein said serum or medium has been treated to remove low molecular weight molecules, such as dialyzed serum. The medium may comprise at least or up to 1, 2, 3, 4, 5, 6, 7, 8, 9, 10, 15, 20, 25, 30, 35, 40, 45, 50, 55, 60, 65, 70, 75, 80, 85, 90, 95, 99% dialyzed serum or any intermediate ranges or numbers. Alternatively, the medium may essentially free of serum or serum components.

The cell population may have at least 50, 60, 70, 80, 90, 91, 92, 93, 94, 95, 96, 97, 98, 99, 99.5, 99.9% cardiomyocytes or any intermediate range or numbers. In a particular aspect, the population may comprise at least 90% or 95% cardiomyocytes. The population may be essentially free of contaminating cells such as fibroblasts or undifferentiated pluripotent stem cells. To facilitate isolation, the cardiomyocytes may express at least one selectable or screenable transgene under the control of a cardiomyocyte-specific promoter. In a further aspect, the cardiomyocytes are mouse or human cardiomyocytes. In a particular aspect, the cardiomyocytes may be cryopreserved cardiomyocytes.

The medium may comprise sugar or be essentially free of sugar. The medium may comprise glucose or be essentially free of glucose. In particular aspects, the medium may comprise galactose, for example, about 1 to 20 mM or any range derivable therein. The medium may further comprise pyruvate or pyruvic acid, such as about 0.1 to 10 mM pyruvate or pyruvic acid. In the aspects of culturing cardiomyocytes, the medium may be a maintenance medium. For example, a maintenance medium may comprise galactose, pyruvate, and dialyzed serum, such as 10 mM galactose, 1 mM pyruvate and 10% dialyzed serum.

Preferably, the cardiomyocytes used herein may be previously purified. The purified population of cardiomyocytes may be essentially free of non-cardiomyocyte cells. A cell population "essentially free" of non-cardiomyocyte cells refers to a cell population that contains up to or less than about 1%, 0.9, 0.8, 0.7, 0.6, 0.5, 0.4, 0.3, 0.2, or 0.1, 0.01% (or any range derivable therein) non-cardiomyocyte cells, including a cell population that has 100% cardiomyocytes. In certain further embodiments, the invention involves a cardiomyocyte cell population that comprises at most or about 20, 15, 10, 9, 8, 7, 6, 5, 4, 3, 2, 1, 0.9, 0.8, 0.7, 0.6, 0.5, 0.4, 0.3, 0.2, or 0.1% (or any range derivable therein) non-cardiomyocyte cells. Exemplary non-cardiomyocyte cells that tend to contaminate pure cardiomyocyte populations include fibroblasts, undifferentiated cells and other non-cardiomyocyte cells.

Culturing of cardiomyocytes in the media as described herein maintains the purity of cardiomyocytes; it is contemplated that to achieve such advantages the cardiomyocytes as described herein may be cultured in the medium for at least or about 2, 3, 4, 5, 6 days, 1, 2, 3, 5, 6, 7, 8, 9, 10, 11, 12 weeks, 1, 2, 3, 4, 5, 6, 7, 8, 9, 11 months, 1, 2, 3, 4, 5 years or any range derivable therein. Specifically, the population of cardiomyocytes may maintain the purify for at least seven months.

For maintaining the purity of a cardiomyocyte population, there may be provided a method comprising: a) obtaining a first composition comprising a cell population of at least 90% cardiomyocytes and a medium that may contain serum, wherein said serum or medium has been treated to remove low molecular weight molecules, or a second composition comprising a second cell population of at least 90% cardiomyocytes and a medium essentially free of serum; and b) culturing said first or second composition. The culturing may last for at least 8 hours, 16 hours, one, two, three, four, five, six or seven days or any intermediate numbers. In a particular aspect, the first or second composition maintains the purity of cardiomyocytes in the culturing.

The method may further comprise contacting cardiomyocytes in the first or second composition with a compound and measuring beating frequency and/or field potential duration of the cardiomyocytes. In particular aspects, the compound may modulate the ion channel activity, beating frequency and/or field potential duration of the cardiomyocytes. For example, the compound that modulates beating frequency may be tetrodotoxin (Octahydro-12-(hydroxymethyl)-2-imino-5,9:7,10a-dimethano-10aH-[1,3]dioxocino[6,5-d]pyrimidine-4,7,10,11,12-pentol) or isoproterenol; the compound that modulates field potential duration may be E-4031 ((1-[2-(6-methyl-2-pyridyl)ethyl]-4-(4-methylsulfonyl-aminobenzoyl)piperidine)) or terfenadine ((RS)-1-(4-tert-butylphenyl)-4-{4-[hydroxy(diphenyl)methyl]piperidin-1-yl}-butan-1-ol).

The method may also comprise cryopreserving cardiomyocytes in the first or second composition prior to the culturing. The method may also comprise purifying cardiomyocytes differentiated from a stem cell or trans-differentiated from a non-cardiomyocyte cell in vitro to obtain cardiomyocytes in the first or second composition.

"Maintaining" the cardiomyocyte purity refers to the purity of cardiomyocytes does not decrease significantly over time, preferably at most or about 10, 9, 8, 7, 6, 5, 4, 3, 2, 1% reduction in the cell purity or homogeneity of the cardiomyocyte population, or any range derivable therein. "Purity" of cardiomyocytes, as used herein, refers to the percentage of cardiomyocytes in a given culture condition. This could be determined by detection of cardiomyocytes based on the expression of endogenous cardiomyocyte marker or transgenic gene marker under the control of a cardiomyocyte-specific promoter. For example, as shown in the Examples, the purity could be measured by quantifying the percentage of RFP positive cells in cardiomyocyte cultures derived from an iPS cell line that expresses RFP driven by a cardiomyocyte-specific promoter or by quantifying the percentage of cardiac troponin T positive cells in cardiomyocyte cultures The inventors have further observed that the culturing of cardiomyocytes in media formulations in accordance with the invention has a profound and reproducible effect on both the beating frequency and beating rate oscillation, and indeed effect both an increase in beating rate and a concomitant decrease in beating rate oscillation (reduced fluctuation or variation in heart beat rate). Thus, the present invention further includes a method of increasing heart beat rate as well as a method of decreasing heart rate oscillation (i.e., enhancing heart rate stability) by culturing cardiomyocyte populations in the media of the present invention.

In still further aspects of the invention, there may be provided a method for testing the effect of a compound on cardiomyocytes, comprising: a) contacting cardiomyocytes with a compound, wherein the cardiomyocytes are cultured in a medium that (i) is essentially free of serum; or (ii) contains serum, wherein the serum or medium has been treated to remove low molecular weight molecules (including low molecular growth factors); and b) measuring beating frequency and/or field potential duration of the cardiomyocytes. The method of measuring may comprise the use of multi-electrode array (MEA).

For enhancing the effect of compounds that may modulate cardiac activity, the cardiomyocytes described herein may be contacted with a compound that modulates cell viability or function in the medium as described herein. Such a compound may modulate the ion channel activity, such as potassium channels or sodium channels. In particularly, the compound may modulate beating frequency, such as tetrodotoxin or isoproterenol, or modulate field potential duration, like E-4031 or terfenadine.

In certain aspects, there may be provided a composition comprising a population of cardiomyocytes and a medium. The population of cardiomyocytes may comprise non-cardiomyocyte cells, such as fibroblasts or undifferentiated cells. The medium may comprise galactose, pyruvate and be essentially free of serum. In other aspects, the medium may comprise galactose, pyruvate and dialyzed serum. The medium may comprise glucose or be essentially free of glucose. The cardiomyocytes may be previously purified; for example, they comprise up to 10, 9, 8, 7, 6, 5, 4, 3, 2, 1% or any intermediate range of non-cardiomyocytes or are essentially free of non-cardiomyocyte cells.

The cardiomyocyte population may be purified, isolated or enriched. The purification, isolation or enrichment may comprise the use of endogenous or exogenous markers specifically expressed in cardiomyocytes. For example, the cardiomyocyte may express one or more selectable or screenable transgenes. For example, the transgene may be a selectable or screenable marker under a cardiomyocyte-specific promoter, such as a promoter of MYH6 (alpha myosin heavy chain) gene. Such a marker may include an antigenic epitope, a fluorescent protein-encoding gene or an antibiotic resistance gene. In certain aspects, the population of cardiomyocytes may be isolated based on expression of the transgene. The isolation of a cardiomyocyte population may be any method known in the art, such as fluorescence sorting or magnetic sorting. The purity of cardiomyocytes may be based on the expression of transgene that specifically expresses in cardiomyocytes.

In certain aspects, the population of cardiomyocytes may have been preserved prior to the culturing in the medium described above. The cardiomyocytes may comprise human cardiomyocytes or cardiomyocytes from different sources, such as any other mammals, like primates, dogs, cats, or mice. The cardiomyocytes may be directly isolated from a subject or may be differentiated from a stem cell or trans-differentiated from a non-cardiomyocyte cell in vitro. Such a stem cell could be a pluripotent stem cell or a tissue stem cell, such as a cardiac stem cell or a non-cardiac lineage stem cell or progenitor cell. The pluripotent stem cell may include an induced pluripotent stem cell, an embryonic stem cell, or a pluripotent stem cell derived by somatic cell nuclear transfer.

In certain aspects, the medium may be essentially free of serum, or more particularly, chemically defined. In other aspects, the medium contains serum but the serum or the medium has been treated to remove low molecular weight molecules, particularly low molecular weight growth factors in the serum. Particularly, the medium or the serum may be essentially free of low molecular weight molecules or may be essentially free of low molecular weight serum growth factors and other components.

In a further aspect, the medium may contain glucose. The glucose in the medium may be at least or about 1, 2, 3, 4, 5, 6, 7, 8, 9, 10, 15, 20, 25, 50, 100, 200, 300, 400, 500, 600, 700, 800, 900 μM or 1, 2, 3, 4, 5, 5.5, 6, 7, 8, 9, 10 mM.

In other aspects, the medium may be essentially free of glucose. For providing an energy source other than glucose, the medium may comprise a compound capable of forming a high energy phosphate bond, an acyl group carrier molecule, or a cardiomyocyte calcium channel modulator. For example, the medium may comprise creatine, carnitine, or taurine. In a further aspect, the medium may comprise insulin.

For providing a carbon and/or energy source other than glucose, the medium may comprise galactose, fructose, mannose, sucrose, maltose, lactose, trehalose, turanose, pyruvate, pyruvic acid, glutamine, glutamic acid, aspartate, aspartic acid, lactate, lactic acid, or a combination thereof. In a particular aspect, the medium may comprise galactose. The galactose in the medium may be at least or about 1, 2, 3, 4, 5, 6, 7, 8, 9, 10, 15, 20, 25, 50 mM or any range derivable therein.

The medium may also comprise pyruvate or pyruvic acid. The pyruvate or pyruvic acid in the medium may be at least or about 0.01, 0.05, 0.1, 0.5, 1, 2, 3, 4, 5, 6, 7, 8, 9, 10 mM or any range derivable therein.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Cardiomyocytes cultured in control medium (Cardiac Maintenance Medium: CMM) or serum free glucose free (SFGF) medium maintain similar cardiomyocyte viability when cultured for 14 days. FIG. 1B. Purified cardiomyocytes cultured in CMM demonstrate a loss of purity (<90%) after 14 days. Cardiomyocytes cultured in SFGF medium maintain a higher purity (>99%).

FIG. 2A. Cardiomyocytes cultured in CMM or in glucose free medium supplemented with dialyzed serum, sodium pyruvate, and galactose (DS-CMM) maintain similar cardiomyocyte viability when cultured for 14 days. FIG. 2B. Purified cardiomyocytes cultured in CMM demonstrate a loss of purity (<90%) after 14 days. Cardiomyocytes cultured in the DS-CMM medium maintain a higher purity (>99%). FIG. 2C. Cryopreserved cardiomyocytes were cultured in DS-CMM for 210 days. Purity was assayed at thaw, 7 days, and 210 days with no significant change in purity.

FIG. 5A. DMEM culture medium containing dialyzed serum but lacking glucose (iCMM, also known as DS-CMM) resulted in cultures with significantly higher cardiomyocyte purity compared to glucose containing DMEM culture media containing dialyzed serum. FIG. 5B. Lack of glucose in normal serum containing DMEM medium increases cardiomyocyte purity of the cell culture.

DESCRIPTION OF ILLUSTRATIVE EMBODIMENTS

I. Introduction

Figures 1A, 1B:
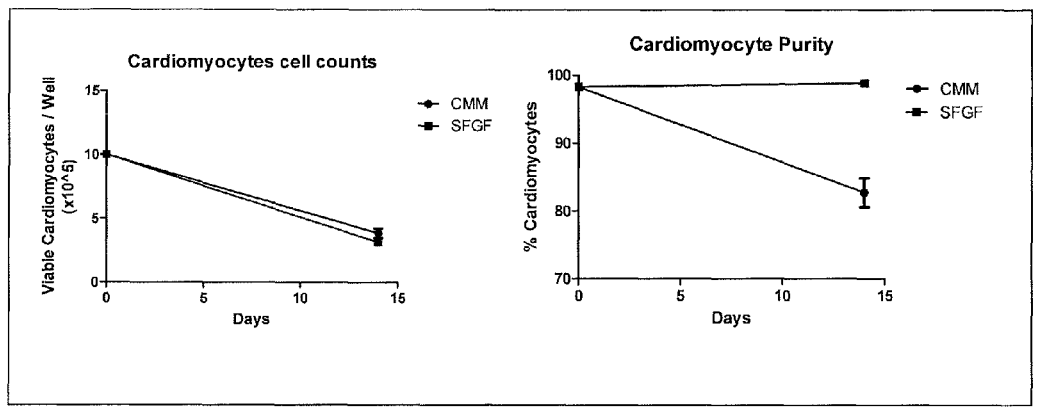
FIGS. 1A-1B: Serum free glucose free medium maintains cardiomyocyte purity in vitro.

The invention is in part based on the finding that serum-free or dialyzed serum-containing media could be designed to retard the growth of non-cardiomyocyte cells in a cardiomyocyte population while maintaining a healthy cardiomyocyte population. Even within a substantially pure cardiomyocyte population, a low percentage of contaminating cells may be present. Under standard serum-containing culturing conditions, some proportion of contaminating cells could proliferate at a faster rate than the cardiomyocytes and may overtake the whole cell population. In some embodiments, media conditions of the present invention may also improve some functional properties of cardiomyocytes.

Further advances in the culturing of cardiomyocyte cell populations are also described below. The remarkable uniformity and functional properties of the cells maintained according to this disclosure make them valuable for studying cardiac tissue in vitro, and for developing new therapeutic modalities for regeneration of cardiac tissue in the treatment of heart disease.

II. Definitions

"Pluripotency" refers to a stem cell that has the potential to differentiate into all cells constituting one or more tissues or organs, for example, any of the three germ layers: endoderm (interior stomach lining, gastrointestinal tract, the lungs), mesoderm (muscle, bone, blood, urogenital), or ectoderm (epidermal tissues and nervous system). "Pluripotent stem cells" used herein refer to cells that can differentiate into cells derived from any of the three germ layers, for example, descendants of totipotent cells or induced pluripotent stem cells.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by introducing or contacting reprogramming factors.

"Embryonic stem (ES) cells" are pluripotent stem cells derived from early embryos.

"Cardiomyocytes" refers generally to any cardiomyocyte lineage cells, and can be taken to apply to cells at any stage of cardiomyocyte ontogeny without any restriction, unless otherwise specified. For example, cardiomyocytes may include both cardiomyocyte precursor cells and mature cardiomyocytes.

A "gene," "polynucleotide," "coding region," "sequence," "segment," or "fragment," which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "transgene," refers to a gene, nucleic acid, or polynucleotide which has been introduced into the cell or organism by artificial or natural means, such as an exogenous nucleic acid. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

Below are abbreviations as well as general descriptions for media types referenced in the Figures and elsewhere herein. More detailed descriptions for media compositions and preparations thereof are found in the specific embodiments.

Reference Table for Media Types:

| Abbreviations | Media Names | General Description |
|---|---|---|
| CMM or DMEM, Normal Serum | Cardiac Maintenance Medium | DMEM with fetal bovine serum added (5.5 mM glucose in total medium) |
| iCMM or DS-CMM | iCell Cardiac Maintenance Medium or DMEM - Glucose, Dialyzed Serum | Modified DMEM without sodium pyruvate or glucose; dialyzed fetal bovine serum added; sodium pyruvate and galactose added (~0 mM Glucose in total medium) |
| DMEM - Glucose, Normal Serum | same | Modified DMEM without sodium pyruvate or glucose; normal fetal bovine serum added; sodium pyruvate and galactose added (0.55 mM glucose in total medium) |
| DMEM, Dialyzed Serum | same | DMEM with dialyzed fetal bovine serum (4.95 mM glucose in total medium) |
| FBS + Media | same | SFGF Medium with fetal bovine serum added |
| SFGF medium | Serum Free Glucose Free medium | Modified DMEM without sodium pyruvate or glucose; no fetal bovine serum added; sodium pyruvate added |

III. Cardiomyocyte Culturing

The culturing conditions according to certain aspects of the present invention could be appropriately defined depending on the medium used. The medium can be prepared using a medium to be used for culturing animal cells as its basal medium. As the basal medium, any of TeSR, BME, BGJb, CMRL 1066, Glasgow MEM, Improved MEM Zinc Option, IMDM, Medium 199, Eagle MEM, αMEM, DMEM, Ham, RPMI 1640, and Fischer's media, as well as any combinations thereof, can be used, but the medium is not particularly limited thereto as far as it can be used for culturing animal cells.

The medium can be a serum-containing or serum-free medium. The serum-free medium refers to a medium with essentially no serum or serum-derived components. The serum-free medium may also be essentially free of blood-derived components or animal tissue-derived components (such as animal tissue-derived growth factors), especially growth factors or serum components with molecular weights up to about 1, 2, 3, 4, 5, 6, 7, 8, 9, 10, 15, 20, 25, 30 kD or any range derivable therefrom.

Most cells grown in culture require a serum component of the growth medium to maintain their proliferative capacity. While whole serum is permissible for routine purposes, studies involving nutritional parameters or incorporation of labeled material require that the constituent under study be removed from the serum. The most commonly used method for removal of these constituents is dialysis of whole serum. For dialysis by diafiltration, serum is circulated through a hollow-fiber by the concentration method. The filtrate, however, is replaced by the addition of physiological saline to the serum. For example, dialysis removes many small molecules from fetal bovine serum (FBS) such as glucose, salts and some non-protein bound serum molecules. This process may not remove hormones that are serum bound but it may reduce growth promotion capabilities for some cell types. The dialysis process could be done by ultra filtration with a 10,000 molecular weight cut-off membrane.

The medium may contain or may not contain any alternatives to serum. The alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolglycerol, or equivalents thereto. The alternatives to serum can be prepared by the method disclosed in International Publication No. 98/30679, for example. Alternatively, any commercially available materials can be used for more convenience. The commercially available materials include knockout Serum Replacement (KSR), Chemically-defined Lipid concentrated (Gibco), and Glutamax (Gibco).

Preferably, the medium may be chemically defined, which refers to a medium essentially free of animal-derived components. For example, the medium may comprise recombinant growth factors or proteins, for example, recombinant albumin.

The medium can also contain fatty acids or lipids, amino acids (such as non-essential amino acids), vitamin(s), growth factors, cytokines, antioxidant substances, 2-mercaptoethanol, pyruvic acid, buffering agents, and inorganic salts. The concentration of 2-mercaptoethanol can be, for example, about 0.05 to 1.0 mM, and particularly about 0.1 to 0.5 mM, but the concentration is particularly not limited thereto as long as it is appropriate for culturing the cell(s).

A culture vessel used for culturing the cardiomyocytes can include, but is particularly not limited to: flask, flask for tissue culture, dish, petri dish, dish for tissue culture, multi dish, micro plate, micro-well plate, multi plate, multi-well plate, micro slide, chamber slide, tube, tray, CellSTACK® Chambers, culture bag, and roller bottle, as long as it is capable of culturing the cardiomyocytes therein. The cardiomyocytes may be cultured in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, 2000 ml or any range derivable therein, depending on the needs of the culture. In a certain embodiment, the culture vessel may be a bioreactor, which may refer to any device or system that supports a biologically active environment. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

The culture vessel can be cellular adhesive or non-adhesive and selected depending on the purpose. The cellular adhesive culture vessel can be coated with any of substrates for cell adhesion such as extracellular matrix (ECM) to improve the adhesiveness of the vessel surface to the cells. The substrate for cell adhesion can be any material intended to attach stem cells or feeder cells (if used). The substrate for cell adhesion includes collagen, gelatin, poly-L-lysine, poly-D-lysine, laminin, and fibronectin and mixtures thereof for example Matrigel™, and lysed cell membrane preparations (Klimanskaya et al., 2005).

Other culturing conditions can be appropriately defined. For example, the culturing temperature can be about 30 to 40° C., for example, at least or about 31, 32, 33, 34, 35, 36, 37, 38, 39° C. but particularly not limited to them. The $CO_2$ concentration can be about 1 to 10%, for example, about 2 to 5%, or any range derivable therein. The oxygen tension can be at least or about 1, 5, 8, 10, 20%, or any range derivable therein.

IV. Cardiomyocyte Preparation

Cardiomyocytes in certain aspects of the present invention could be prepared by differentiation of stem cells such as induced pluripotent stem cells or cardiac stem cells, or trans-differentiation of non-cardiac cells, including other tissue stem cells. Differentiation of pluripotent stem cells can be induced in a variety of manners, such as in attached colonies or by formation of cell aggregates, e.g., in low-attachment environment, wherein those aggregates are referred to as embryoid bodies (EBs). The molecular and cellular morphogenic signals and events within EBs mimic many aspects of the natural ontogeny of such cells in a developing embryo.

Alternatively, cardiomyocytes could be prepared by direct differentiation of pluripotent stem cells. "Direct differentiation" refers to a process for differentiating pluripotent stem cells into progeny that are enriched for cells of a particular tissue type without forming embryoid bodies (cell aggregates) as an intermediate. This may be done when the cells are plated on a solid substrate, although plating is not necessarily required if not explicitly specified. Direct differentiation is effected by culturing in a growth environment of media components, soluble factors, insoluble components in suspension or on the vessel wall, and other ingredients that accomplish the objective of directing the cells towards the desired tissue type.

Embryoid bodies (EBs) are aggregates of cells derived from pluripotent stem cells, such as ES cells or iPS cells, and have been studied for years with mouse embryonic stem cells. In order to recapitulate some of the cues inherent to in vivo differentiation, certain aspects of the invention may employ three-dimensional aggregates (i.e., embryoid bodies) as an intermediate step. Upon aggregation, differentiation is initiated and the cells begin to a limited extent to recapitulate embryonic development. Though they cannot form trophectodermal tissue (which includes the placenta), cells of virtually every other type present in the organism can develop. The present invention may further promote cardiac differentiation following aggregate formation.

Cell aggregation may be imposed by hanging drop, plating upon non-tissue culture treated plates or spinner flasks; either method prevents cells from adhering to a surface to form the typical colony growth. Pluripotent stem cells may be seeded into aggregate promotion medium using any method known in the art of cell culture. For example, pluripotent stem cells may be seeded as a single colony or clonal group into aggregate promotion medium, and pluripotent stem cells may also be seeded as essentially individual cells. In some embodiments, pluripotent stem cells are dissociated into essentially individual cells using mechanical or enzymatic methods known in the art. By way of non-limiting example, pluripotent stem cells may be exposed to a proteolytic enzyme which disrupts the connections between cells and the culturing surface and between the cells themselves. Enzymes which may be used to individualize pluripotent stem cells for aggregate formation and differentiation may include, but are not limited to, trypsin, in its various commercial formulations, such as TrypLE, or a mixture of enzymes such as Accutase®.

In certain embodiments, pluripotent cells may be added or seeded as essentially individual (or dispersed) cells to a culturing medium for culture formation on a culture surface. The culturing medium into which cells are seeded may comprise TeSR medium or mTeSR medium and a survival factor. For example, dispersed pluripotent cells are seeded into a culturing medium at a density of from about $10^4$ cells/ml to about $10^{10}$ cells/ml. More particularly, pluripotent cells are seeded at a density of from about $10^5$ cells/ml to about $10^7$ cells/ml, or about $0.5 \times 10^6$ cells/ml to about $3 \times 10^6$ cells/ml. In these embodiments, a culturing surface may be comprised of essentially any material which is compatible with standard aseptic cell culture methods in the art, for example, a non-adherent surface. A culturing surface may additionally comprise a matrix component as described herein. In certain embodiments, a matrix component may be applied to a culturing surface before contacting the surface with cells and medium.

Cardiomyocyte lineage cells can be obtained from undifferentiated stem cells by culturing or differentiating in a special growth environment that enriches for cells with the desired phenotype (either by outgrowth of the desired cells, or by inhibition or killing of other cell types).

In certain aspects, the iPS cells may be differentiated into cardiac cells incorporating the disclosed methods. Differentiation can be initiated by forming embryoid bodies or aggregates as described above: for example, by overgrowth of a pluripotent stem cell culture, or by culturing pluripotent stem cells in suspension in culture vessels having a substrate with low adhesion properties which allows EB formation. Pluripotent stem cells could be harvested by brief collagenase digestion, dissociated into clusters, and plated in non-adherent cell culture plates (WO 01/51616; U.S. Pat. No. 6,602, 711, incorporated by reference). Optionally, the EBs can be produced encapsulated in alginate or other suitable nutrient-permeable matrix, which may help improve the uniformity of EB diameter and consistency of the cells produced (WO 03/004626, Zandstra et al., incorporated by reference). Whether or not the process involves EB formation, using a medium that contains serum or serum equivalent promotes foci of contracting cells of the cardiomyocyte lineage: for example, about 20% fetal bovine serum, or a serum supplement such as B27 or N2 in a suitable growth medium such as RPMI. More exemplary methods of cardiac differentiation may include embryoid body (EB) methods (Zhang et al., 2009, which is incorporated by reference), OP9 stroma cell methods (Narazaki, et al., 2008, which is incorporated by reference), or growth factor/chemical methods (see U.S. Patent Publication Nos. 20080038820, 20080226558, 20080254003 and 20090047739, all incorporated herein by reference in their entirety).

To promote the cardiomyocyte phenotype, the cells can be cultured with factors and factor combinations that enhance proliferation or survival of cardiomyocyte type cells, or inhibit the growth of other cell types. The effect may be due to a direct effect on the cell itself, or due to an effect on another cell type, which in turn enhances cardiomyocyte formation. For example, factors that induce the formation of hypoblast or epiblast equivalent cells, or cause these cells to produce their own cardiac promoting elements, all come within the rubric of cardiotropic factors.

For example, induction medium for cardiac differentiation may include, but is not limited to, precardiac explants, pre-cardiac mesoderm conditioned medium, and mesoderm secreted growth factors such as HGF.

Additional factors thought to induce differentiation of pluripotent stem cells into cells of the mesoderm layer, or facilitate further differentiation into cardiomyocyte lineage cells include the following:

Transforming Growth Factor beta-related ligands (exemplified by TGF-β1, TGF-β2, TGF-β3 and other members of the TGF-β superfamily illustrated below). Ligands bind a TGF-β receptor activate Type I and Type II serine kinases and cause phosphorylation of the SMAD effector.

Morphogens like Activin A and Activin B (members of the TGF-β superfamily).

Insulin-like growth factors (such as IGF I and IGF II).

Bone morphogenic proteins (members of the TGF-β superfamily, exemplified by BMP-2 and BMP-4).

Fibroblast growth factors (exemplified by bFGF, FGF-4, and FGF-8), other ligands that activate cytosolic kinase raf-1 and mitogen-activated proteins kinase (MAPK), and other mitogens such as epidermal growth factor (EGF).

Nucleotide analogs that affect DNA methylation and altering expression of cardiomyocyte-related genes (e.g., 5-aza-deoxy-cytidine).

The pituitary hormone oxytocin, or nitric oxide (NO).

Specific antibodies or synthetic compounds with agonist activity for the same receptors.

Exemplary effective combinations of cardiotropic agents include use of a morphogen like Activin A and a plurality of growth factors, such as those included in the TGF-β and IGF families during the early commitment stage, optionally supplemented with additional cardiotropins such as one or more fibroblast growth factors, bone morphogenic proteins, and platelet-derived growth factors.

It was found that omitting factors such as insulin-like growth factor II (IGF II) and related molecules from the final stages of in vitro differentiation actually increase the levels of cardiac gene expression. In unrelated studies, IGF II has been found to decrease the levels of GSK3β in fibroblasts (Scalia et al., 2001). IGF II may therefore potentiate the effects of Wnt proteins present in the culture medium or secreted by the cells. Wnt proteins normally stabilize and cause nuclear translocation of a cytoplasmic molecule, β-catenin, which comprises a portion of the transcription factor TCF. This changes transcriptional activity of multiple genes. In the absence of Wnt, β-catenin is phosphorylated by the kinase GSK3β, which both destabilizes β-catenin and keeps it in the cytoplasm.

Since Wnt activators like IGF II apparently limit cardiomyocyte differentiation, certain aspects of this invention may include culturing with Wnt antagonists to increase the extent or proportion of cardiomyocyte differentiation of pluripotent stem cells. Wnt signaling can be inhibited by injection of synthetic mRNA encoding either DKK-1 or Crescent (secreted proteins that bind and inactivate Wnts) (Schneider et al., 2001), or by infection with a retrovirus encoding DKK-1 (Marvin et al., 2001). Alternatively, the Wnt pathway can be inhibited by increasing the activity of the kinase GSK3β, for example, by culturing the cells with factors such as IL-6 or glucocorticoids.

In a certain embodiment, FGF or a combination of FGF and HGF are used to culture pluripotent stem cells, cell aggregates, or differentiated stem cells, which may promote cardiac induction of stem cells. For example, FGF may be added at a concentration of at least or about 5, 10, 15, 20, 25, 30, 35, 40, 45, 50, 55, 60, 65, 70, 75, 80, 85, 90, 95, 100, 150, 180, 200, 250 ng/ml or any range derivable therein. Optionally hepatic growth factor (HGF) may also be included, for example at a concentration of at least or about 5, 10, 15, 20, 25, 30, 35, 40, 45, 50, 55, 60, 65, 70, 75, 80, 85, 90, 95, 100, 150, 180, 200, 250 ng/ml or any range derivable therein.

V. Sources of Pluripotent Stem Cells

In certain aspects of the invention, cardiomyocytes could be derived from pluripotent stem cells in vitro.

The term "pluripotent stem cell" refers to a cell capable of giving rise to cells of all three germinal layers, that is, endoderm, mesoderm and ectoderm. Although in theory a pluripotent stem cell can differentiate into any cell of the body, the experimental determination of pluripotency is typically based on differentiation of a pluripotent cell into several cell types of each germinal layer. In some embodiments of the present invention, a pluripotent stem cell is an embryonic stem (ES) cell derived from the inner cell mass of a blastocyst. In other embodiments, the pluripotent stem cell is an induced pluripotent stem cell derived by reprogramming somatic cells. In certain embodiments, the pluripotent stem cell is an embryonic stem cell derived by somatic cell nuclear transfer.

A. Embryonic Stem Cells

Embryonic stem (ES) cells are pluripotent cells derived from the inner cell mass of a blastocyst. ES cells can be isolated by removing the outer trophectoderm layer of a developing embryo, then culturing the inner mass cells on a feeder layer of non-growing cells. Under appropriate conditions, colonies of proliferating, undifferentiated ES cells are produced. The colonies can be removed, dissociated into individual cells, then replated on a fresh feeder layer. The replated cells can continue to proliferate, producing new colonies of undifferentiated ES cells. The new colonies can then be removed, dissociated, replated again and allowed to grow. This process of "subculturing" or "passaging" undifferentiated ES cells can be repeated a number of times to produce cell lines containing undifferentiated ES cells (U.S. Pat. Nos. 5,843,780; 6,200,806; 7,029,913). A "primary cell culture" is a culture of cells directly obtained from a tissue such as the inner cell mass of a blastocyst. A "subculture" is any culture derived from the primary cell culture.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be obtained from blastocysts using previously described methods (Thomson et al., 1995; Thomson and Marshall, 1998; Reubinoff et al, 2000.) In one method, day-5 human blastocysts are exposed to rabbit anti-human spleen cell antiserum, then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as Matrigel™ or laminin in the presence of "conditioned" medium containing basic fibroblast growth factor (Xu et al., 2001). The medium is previously conditioned by coculturing with fibroblasts.

Methods for the isolation of rhesus monkey and common marmoset ES cells are also known (Thomson, and Marshall, 1998; Thomson et al., 1995; Thomson and Odorico, 2000).

Another source of ES cells are established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13 and H14 were established by Thompson et al. In addition, subclones H9.1 and H9.2 of the H9 line have been developed. It is anticipated that virtually any ES or stem cell line known in the art and may be used with the present invention, such as, e.g., those described in Yu and Thompson, 2008, which is incorporated herein by reference.

The source of ES cells for use in connection with the present invention can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

B. Induced Pluripotent Stem Cells

Induced pluripotent stem (iPS) cells are cells which have the characteristics of ES cells but are obtained by the reprogramming of differentiated somatic cells. Induced pluripotent stem cells have been obtained by various methods. In one method, adult human dermal fibroblasts are transfected with transcription factors Oct4, Sox2, c-Myc and Klf4 using retroviral transduction (Takahashi et al., 2007). The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF.

Based on cell characteristics, cells of the ES cell-like colonies are induced pluripotent stem cells. The induced pluripotent stem cells are morphologically similar to human ES cells, and express various human ES cell markers. Also, when grown under conditions that are known to result in differentiation of human ES cells, the induced pluripotent stem cells differentiate accordingly. For example, the induced pluripotent stem cells can differentiate into cells having neuronal structures and neuronal markers. It is anticipated that virtually any iPS cells or cell lines may be used with the present invention, including, e.g., those described in Yu and Thompson, 2008.

In another method, human fetal or newborn fibroblasts are transfected with four genes, Oct4, Sox2, Nanog and Lin28 using lentivirus transduction (Yu et al., 2007). At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage and gut epithelium after injection into mice.

Methods of preparing induced pluripotent stem cells from mouse are also known (Takahashi and Yamanaka, 2006). Induction of iPS cells typically require the expression of or exposure to at least one member from Sox family and at least one member from Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog and, optionally, Lin-28; or comprising Sox-2, Oct4, Klf and, optionally, c-Myc.

IPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of embryonic stem cells can be confirmed by injecting approximately $0.5-10 \times 10^6$ cells into the rear leg muscles of 8-12 week old male SCID mice. Teratomas develop that demonstrate at least one cell type of each of the three germ layers.

In certain aspects of the present invention, iPS cells are made from reprogramming somatic cells using reprogramming factors comprising Oct family member and a Sox family member, such as Oct4 and Sox2 in combination with Klf or Nanog as describe above. The somatic cell in the present invention may be any somatic cell that can be induced to pluripotency, such as a fibroblast, a keratinocyte, a hematopoietic cell, a mesenchymal cell, a liver cell, a stomach cell, or a β cell. In a certain aspect, T cells may also be used as source of somatic cells for reprogramming (see U.S. Application No. 61/184,546, incorporated herein by reference).

Reprogramming factors may be expressed from expression cassettes comprised in one or more vectors, such as an integrating vector or an episomal vector, such as a EBV element-based system (see U.S. application Ser. No. 12/478,154, incorporated herein by reference; Yu et al., 2009). In a further aspect, reprogramming proteins could be introduced directly into somatic cells by protein transduction (see U.S. application Ser. No. 12/723,063, incorporated herein by reference) or RNA transfection (see U.S. application Ser. No. 12/735,060).

C. Embryonic Stem Cells Derived by Somatic Cell Nuclear Transfer

Pluripotent stem cells can be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by electrofusion (Byrne et al., 2007). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo. As used herein, the term "ES cells" refers to embryonic stem cells derived from embryos containing fertilized nuclei. ES cells are distinguished from embryonic stem cells produced by nuclear transfer, which are referred to as "embryonic stem cells derived by somatic cell nuclear transfer."

VI. Characterization of Cardiomyocytes

The cardiomyocyte can be characterized according to a number of phenotypic criteria, for example, the cardiomyocytes can purified or isolated, or alternatively, the purity of cardiomyocytes in a culture can be determined based on detection of cardiomyocytes in the culture. Cardiomyocytes derived from stem cells, such as pluripotent stem cell, have morphological characteristics of cardiomyocytes from other sources. They can be spindle, round, triangular or multi-angular shaped, and they may show striations characteristic of sarcomeric structures detectable by immunostaining. They may form flattened sheets of cells, or aggregates that stay attached to the substrate or float in suspension, showing typical sarcomeres and atrial granules when examined by electron microscopy.

For example, the purity of cardiomyocytes may be determined by detecting cardiomyocytes which express an exogenous marker gene under the control of a promoter of a cardiomyocyte-specific marker or which expression an endogenous cardiomyocyte-specific marker. In a further aspect, such detection may be used to isolate or purify the cardiomyocytes for a long-term storage in a medium described in certain aspects of the invention.

For example, the cardiomyocyte-specific markers may include:

Cardiac troponin I (cTnI), a subunit of troponin complex that provides a calcium-sensitive molecular switch for the regulation of striated muscle contraction.

Cardiac troponin T (cTnT).

Nkx2.5, a cardiac transcription factor expressed in cardiac mesoderm during early mouse embryonic development, which persists in the developing heart.

Atrial natriuretic factor (ANF), a hormone expressed in developing heart and fetal cardiomyocytes but down-regulated in adults. It is considered a good marker for cardiomyocytes because it is expressed in a highly specific manner in cardiac cells but not skeletal myocytes.

Myosin heavy chain (MHC), particularly the β chain which is cardiac specific

Titin, tropomyosin, α-sarcomeric actinin, and desmin

GATA-4, a transcription factor that is highly expressed in cardiac mesoderm and persists in the developing heart. It regulates many cardiac genes and plays a role in cardiogenesis MEF-2A, MEF-2B, MEF-2C, MEF-2D; transcription factors that are expressed in cardiac mesoderm and persist in developing heart N-cadherin, which mediates adhesion among cardiac cells Connexin 43, which forms the gap junction between cardiomyocytes.

β1-adrenoceptor (β1-AR)

creatine kinase MB (CK-MB) and myoglobin, which are elevated in serum following myocardial infarction α-cardiac actin, early growth response-I, and cyclin D2.

Cardiomyocyte-specific markers can be detected using any suitable immunological technique—such as flow immunocytometry or affinity adsorption for cell-surface markers, immunocytochemistry (for example, of fixed cells or tissue sections) for intracellular or cell-surface markers, Western blot analysis of cellular extracts, and enzyme-linked immunoassay, for cellular extracts or products secreted into the medium. Antibodies that distinguish cardiac markers like cTnI and cTnT from other isoforms are available commercially from suppliers like Sigma and Spectral Diagnostics. Expression of an antigen by a cell is said to be antibody-detectable if a significantly detectable amount of antibody will bind to the antigen in a standard immunocytochemistry or flow cytometry assay, optionally after fixation of the cells, and optionally using a labeled secondary antibody.

The expression of cardiomyocyte-specific gene products can also be detected at the mRNA level by Northern blot analysis, dot-blot hybridization analysis, or by reverse transcriptase initiated polymerase chain reaction (RT-PCR) using sequence-specific primers in standard amplification methods using publicly available sequence data (GenBank). Expression of tissue-specific markers as detected at the protein or mRNA level is considered positive if the level is at least or about 2-, 3-, 4-, 5-, 6-, 7-, 8-, or 9-fold, and more particularly more than 10-, 20-, 30, 40-, or 50-fold above that of a control cell, such as an undifferentiated pluripotent stem cell or other unrelated cell type.

Once markers have been identified on the surface of cells of the desired phenotype, they can be used for immunoselection to further enrich the population by techniques such as immunopanning or antibody-mediated fluorescence-activated cell sorting.

Under appropriate circumstances, pluripotent stem cell-derived cardiomyocytes often show spontaneous periodic contractile activity. This means that when they are cultured in a suitable tissue culture environment with an appropriate $Ca^{2+}$ concentration and electrolyte balance, the cells can be observed to contract across one axis of the cell, and then release from contraction, without having to add any additional components to the culture medium. The contractions are periodic, which means that they repeat on a regular or irregular basis, at a frequency between about 6 and 200 contractions per minute, and often between about 20 and about 90 contractions per minute in normal buffer. Individual cells may show spontaneous periodic contractile activity on their own, or they may show spontaneous periodic contractile activity in concert with neighboring cells in a tissue, cell aggregate, or cultured cell mass.

The contractile activity of the cells can be characterized according to the influence of culture conditions on the nature and frequency of contractions. Compounds that reduce available $Ca^{2+}$ concentration or otherwise interfere with trans-membrane transport of $Ca^{2+}$ often affect contractile activity. For example, the L-type calcium channel blocker diltiazem inhibits contractile activity in a dose-dependent manner. On the other hand, adrenoceptor agonists like isoprenaline and phenylephrine have a positive chronotropic effect. Further characterization of functional properties of the cell can involve characterizing channels for $Na^+$, $K^+$, and $Ca^{2+}$. Electrophysiology can be studied by patch clamp analysis for cardiomyocyte like action potentials.

Functional attributes provide a manner of characterizing cells and their precursors in vitro, but may not be necessary for some of the uses referred to in this disclosure. For example, a mixed cell population enriched for cells bearing some of the markers listed above, but not all of the functional or electrophysiology properties, can be of considerable therapeutic benefit if they are capable of grafting to impaired cardiac tissue, and acquiring in vivo the functional properties needed to supplement cardiac function.

VII. Genetic Alteration of Cells

In certain aspects, the cells of this invention can be made to contain one or more genetic alterations by genetic engineering of the cells either before or after differentiation (US 2002/0168766). A cell is said to be "genetically altered" or "transgenic" when a polynucleotide has been transferred into the cell by any suitable means of artificial manipulation, or where the cell is a progeny of the originally altered cell that has inherited the polynucleotide. For example, the cells can be processed to increase their replication potential by genetically altering the cells to express telomerase reverse transcriptase, either before or after they progress to restricted developmental lineage cells or terminally differentiated cells (US 2003/0022367).

The cells of this invention can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in the differentiated cell type. Of particular interest are cells that are genetically altered to express one or more growth factors of various types such as FGF, cardiotropic factors such as atrial natriuretic factor, cripto, and cardiac transcription regulation factors, such as GATA-4, Nkx2.5, and MEF2-C. Production of these factors at the site of administration may facilitate adoption of the functional phenotype, enhance the beneficial effect of the administered cell, or increase proliferation or activity of host cells neighboring the treatment site.

In certain embodiments of the invention, cells containing a nucleic acid construct of the present invention may be identified in vitro or in vivo by including a marker in an expression vector, such as a selectable or screenable marker. Such markers would confer an identifiable change to the cell permitting easy identification of cells containing the expression vector, or help enrich or identify differentiated cardiac cells by using a cardiomyocyte-specific promoter, such as promoters of cardiac troponin I (cTnI), cardiac troponin T (cTnT), α-myosin heavy chain (MYH6), myosin light chain-2v (MLC-2v), GATA-4, Nkx2.5, N-cadherin, β1-adrenoceptor, the MEF-2 family of transcription factors, creatine kinase MB (CK-MB), myoglobin, or atrial natriuretic factor (ANF).

Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, blasticidin, DHFR, GPT, zeocin and histidinol are useful selectable markers.

In addition to markers conferring a phenotype that allows for the discrimination of transformants based on the implementation of conditions, other types of markers including screenable markers such as GFP, whose basis is colorimetric analysis, are also contemplated.

Examples of such screenable include genes encoding cell surface proteins (e.g., CD4, HA epitope), fluorescent proteins, antigenic determinants and enzymes (e.g., β-galactosidase). The vector containing cells may be isolated, e.g., by FACS using fluorescently-tagged antibodies to the cell surface protein or substrates that can be converted to fluorescent products by a vector encoded enzyme.

In specific embodiments, the screenable marker encodes a fluorescent protein. A broad range of fluorescent protein genetic variants have been developed that feature fluorescence emission spectral profiles spanning almost the entire visible light spectrum (see Table 1 for non-limiting examples). Mutagenesis efforts in the original *Aequorea victoria* jellyfish green fluorescent protein have resulted in new fluorescent probes that range in color from blue to yellow, and are some of the most widely used in vivo reporter molecules in biological research. Longer wavelength fluorescent proteins, emitting in the orange and red spectral regions, have been developed from the marine anemone, *Discosoma striata*, and reef corals belonging to the class Anthozoa.

TABLE 1

Fluorescent Protein Properties

| Protein (Acronym) | Excitation Maximum (nm) | Emission Maximum (nm) | Molar Extinction Coefficient | Quantum Yield | in vivo Structure | Relative Brightness (% of EGFP) |
|---|---|---|---|---|---|---|
| GFP (wt) | 395/475 | 509 | 21,000 | 0.77 | Monomer* | 48 |
| Green Fluorescent Proteins | | | | | | |
| EGFP | 484 | 507 | 56,000 | 0.60 | Monomer* | 100 |
| AcGFP | 480 | 505 | 50,000 | 0.55 | Monomer* | 82 |
| TurboGFP | 482 | 502 | 70,000 | 0.53 | Monomer* | 110 |
| Emerald | 487 | 509 | 57,500 | 0.68 | Monomer* | 116 |
| Azami Green | 492 | 505 | 55,000 | 0.74 | Monomer | 121 |
| ZsGreen | 493 | 505 | 43,000 | 0.91 | Tetramer | 117 |
| Blue Fluorescent Proteins | | | | | | |
| EBFP | 383 | 445 | 29,000 | 0.31 | Monomer* | 27 |
| Sapphire | 399 | 511 | 29,000 | 0.64 | Monomer* | 55 |
| T-Sapphire | 399 | 511 | 44,000 | 0.60 | Monomer* | 79 |
| Cyan Fluorescent Proteins | | | | | | |
| ECFP | 439 | 476 | 32,500 | 0.40 | Monomer* | 39 |
| mCFP | 433 | 475 | 32,500 | 0.40 | Monomer | 39 |
| Cerulean | 433 | 475 | 43,000 | 0.62 | Monomer* | 79 |
| CyPet | 435 | 477 | 35,000 | 0.51 | Monomer* | 53 |
| AmCyan1 | 458 | 489 | 44,000 | 0.24 | Tetramer | 31 |
| Midori-Ishi Cyan | 472 | 495 | 27,300 | 0.90 | Dimer | 73 |
| mTFP1 (Teal) | 462 | 492 | 64,000 | 0.85 | Monomer | 162 |
| Yellow Fluorescent Proteins | | | | | | |
| EYFP | 514 | 527 | 83,400 | 0.61 | Monomer* | 151 |
| Topaz | 514 | 527 | 94,500 | 0.60 | Monomer* | 169 |
| Venus | 515 | 528 | 92,200 | 0.57 | Monomer* | 156 |
| mCitrine | 516 | 529 | 77,000 | 0.76 | Monomer | 174 |
| YPet | 517 | 530 | 104,000 | 0.77 | Monomer* | 238 |
| PhiYFP | 525 | 537 | 124,000 | 0.39 | Monomer* | 144 |
| ZsYellow1 | 529 | 539 | 20,200 | 0.42 | Tetramer | 25 |
| mBanana | 540 | 553 | 6,000 | 0.7 | Monomer | 13 |
| Orange and Red Fluorescent Proteins | | | | | | |
| Kusabira Orange | 548 | 559 | 51,600 | 0.60 | Monomer | 92 |
| mOrange | 548 | 562 | 71,000 | 0.69 | Monomer | 146 |
| dTomato | 554 | 581 | 69,000 | 0.69 | Dimer | 142 |
| dTomato-Tandem | 554 | 581 | 138,000 | 0.69 | Monomer | 283 |
| DsRed | 558 | 583 | 75,000 | 0.79 | Tetramer | 176 |
| DsRed2 | 563 | 582 | 43,800 | 0.55 | Tetramer | 72 |
| DsRed-Express (T1) | 555 | 584 | 38,000 | 0.51 | Tetramer | 58 |
| DsRed-Monomer | 556 | 586 | 35,000 | 0.10 | Monomer | 10 |
| mTangerine | 568 | 585 | 38,000 | 0.30 | Monomer | 34 |
| mStrawberry | 574 | 596 | 90,000 | 0.29 | Monomer | 78 |
| AsRed2 | 576 | 592 | 56,200 | 0.05 | Tetramer | 8 |
| mRFP1 | 584 | 607 | 50,000 | 0.25 | Monomer | 37 |
| JRed | 584 | 610 | 44,000 | 0.20 | Dimer | 26 |
| mCherry | 587 | 610 | 72,000 | 0.22 | Monomer | 47 |
| HcRed1 | 588 | 618 | 20,000 | 0.015 | Dimer | 1 |
| mRaspberry | 598 | 625 | 86,000 | 0.15 | Monomer | 38 |
| HcRed-Tandem | 590 | 637 | 160,000 | 0.04 | Monomer | 19 |
| mPlum | 590 | 649 | 41,000 | 0.10 | Monomer | 12 |
| AQ143 | 595 | 655 | 90,000 | 0.04 | Tetramer | 11 |

*Weak Dimer

Alternatively, screenable enzymes such as chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

VIII. Use of Cultured Cardiomyocytes

Certain aspects of this invention provide a method to culture cells of the cardiomyocyte lineage. The culture method or medium of the present invention could affect functional properties of the cardiomyocytes. For example, the culture medium could facilitate beating rate or reduce the incidence of beating rate oscillations. Such cultured cardiomyocytes may be used for a number of important research, development, and commercial purposes.

Cardiomyocytes of this invention can be used commercially to screen for factors (such as solvents, small molecule drugs, peptides, oligonucleotides) or environmental conditions (such as culture conditions or manipulation) that affect the characteristics of such cells and their various progeny, such as beating frequency or beating rate oscillations. The culture medium as described above may increase beating frequency and reduce the incidence of beating rate oscillations, thereby increasing the stability of beating frequency recordings.

In certain aspects, the cardiomyocytes could be cultured in the medium as described above to facilitate a) normal beating frequency of cardiomyocytes; b) normal field potential duration of beating cardiomyocytes; c) beating frequency of cardiomyocytes treated with compounds that may effect beating frequency; or d) field potential duration of cardiomyocytes treated with compounds that may effect field potential duration.

Beating (contractile) frequency of cardiomyocytes can be modulated by culture media pH, temperature, or a modulator drug. Exemplary non-limiting modulator drugs include catecholamine, a calcium channel blocker, or potassium.

Cardiomyocytes, as well as populations of cardiomyocytes including enriched or selected cardiomyocytes of any developmental, maturation or differentiation stage thereof can be used to screen for or identify cardioactive agents. In various non-limiting embodiments, a cardiomyocyte population used in a screen or identification method includes nodal, sino-atrial or pacemaker cells, mature contractile cardiomyocytes, immature cardiomyocytes (cardioblasts), or a mixed population thereof.

Effect of cell function can be assessed using any standard assay to observe phenotype or activity of cardiomyocytes, such as marker expression, receptor binding, contractile activity, or electrophysiology—either in cell culture or in vivo. Pharmaceutical candidates can also be tested for their effect on contractile activity—such as whether they increase or decrease the extent or frequency of contraction. Where an effect is observed, the concentration of the compound can be titrated to determine the median effective dose ($ED_{50}$).

In certain aspects, cardiomyocytes cultured in the medium according to certain aspects of the invention could be used to measure functional properties of the cardiomyocytes, particularly cardiac specific electrical activity, such as beating frequency or field potential.

Detection of cardiac specific electrical activity of the cells and tissues of the present invention may be effected by monitoring the electrical activity thereof via a multielectrode array. Suitable multielectrode arrays may be obtained from Multi Channel Systems, Reutlingen, Germany. For example, the multielectrode array could be a two-dimensional orthogonal array which includes 60 or more electrodes positioned 100 μm or less apart. In certain aspects, the multielectrode array is configured to obtain data characterizing cardiac specific electrical activity with a frequency greater than a range selected from 1-25 kHz.

Monitoring electrical activity in the cells and tissues of the present invention can be used to provide many different types of important and novel information regarding electrical activity of cells and tissues of the present invention. For example, such monitoring can be used to monitor electrical activity individually at each electrode, or more advantageously, such monitoring can be used to generate electrical activity propagation maps, also termed herein "activation maps", depicting electrical activity as a function of local activation time at each electrode, for example in the form of a color-coded gradient. Such activation maps can be used to depict conduction velocity and conduction directionality of propagative electrical activity, preferably in the form of conduction velocity vectors, of electrical activity propagation over an area of the microelectrode array.

In accordance with certain aspects of the invention, there are also provided methods of screening and identifying cardioactive agents. In one embodiment, a method includes contacting a cardiomyocyte with a test agent; and determining if the test agent modulates an activity or function of cardiomyocytes within the population. A test agent modulating an activity or function of cardiomyocytes within the population identifies the test agent as a cardioactive agent. Exemplary activity or function that can be modulated include contraction or beating, or production of a metabolic product (e.g., production of one or more of urea, creatine or $CO_2$), or intracellular enzyme (e.g., one or more of lactate dehydrogenase, creatine phosphokinase (CPK), creatine kinase (CK) or troponin), or cellular apoptosis, necrosis, death; or de-differentiation, maturation, or division.

Methods of screening and identifying cardioactive agents include those suitable for high throughput screening, which include arrays of cardiomyocyte cells (e.g., microarrays) positioned or placed, optionally at pre-determined locations or addresses. High-throughput robotic or manual handling methods can probe chemical interactions and determine levels of expression of many genes in a short period of time. Techniques have been developed that utilize molecular signals (e.g., fluorophores) and automated analyses that process information at a very rapid rate (see, e.g., Pinhasov et al., 2004). For example, microarray technology has been extensively utilized to probe the interactions of thousands of genes at once, while providing information for specific genes (see, e.g., Mocellin and Rossi, 2007).

Such high-throughput screening methods can identify cardioactive agents. For example, cardiomyocyte cells (e.g., cardiomyoblasts, cardiomyocytes or sino-atrial nodal cells) can be positioned or placed (pre-seeded) on a culture dish, tube, flask, roller bottle or plate (e.g., a single multi-well plate or dish such as an 8, 16, 32, 64, 96, 384 and 1536 multi-well plate or dish), optionally at defined locations, for identification of potentially therapeutic molecules. Libraries that can be screened include, for example, small molecule libraries, siRNA libraries, and adenoviral transfection vectors.

Such high throughput methods are therefore also applicable to predictive toxicology. The use of cardiomyocyte cells (e.g., cardiomyoblasts, cardiomyocytes or sino-atrial nodal cells) positioned or placed (pre-seeded) on a culture dish, tube, flask, roller bottle or plate (e.g., a single multi-well plate or dish such as an 8, 16, 32, 64, 96, 384 and 1536 multi-well plate or dish), optionally at defined locations, for high-throughput or high content screening using small molecule libraries, siRNA libraries, adenoviral transfection vectors, and gene based microarray approaches can identify various therapeutic and cardiac liability targets. Such techniques also allow direct high-throughput measurement of cardiac intervention strategies by means of fluorescent reporter dyes and biomarkers for cell health and morphological phenotype, expression of fluorescent reporter proteins, various FRET approaches and direct measurement of electrophysiological currents in live cells.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Medium Formulations and Preparation

A defined, serum free, glucose free (SFGF) medium was designed to maintain the survival of cardiomyocyte cells grown in vitro. The medium has also been designed to maintain the purity cardiomyocyte cells grown in vitro. Culture medium with standard levels of glucose and normal serum induce outgrowth of the non-cardiomyocyte population. This medium maintains the cardiomyocyte purity of the culture for at least 2 weeks.

The serum free glucose free (SFGF) medium contains:
98.4% DMEM (No Glucose) Invitrogen—11966-025
10 mM Galactose—Sigma G5388
1 mM Sodium Pyruvate—Sigma P4562
5 mM Creatine—Sigma 27890
2 mM Carnitine—Sigma C0283
5 mM Taurine—Sigma T8691
2.5 µM Insulin—Sigma I9278
0.2% Bovine Serum Albumin—Sigma A9576
1 mM L-Glutamine—Invitrogen 21051
1% DPBS—Invitrogen 14190
0.1 mM L-glutamine—Invitrogen 21051
7 µL β-mercaptoethanol—Sigma M7522
SFGF Medium Preparation:

| | MW | Final Concentration | Prepare 1 L |
|---|---|---|---|
| DMEM - Glucose - Pyruvate | N/A | | 830 mL |
| Galactose | 180.16 | 10 mM | 20 mL of 500 mM stock |
| Na Pyruvate | 110.04 | 1 mM | 10 mL of 100 mM stock |
| Creatine | 131.1 | 5 mM | 100 ml of 50 mM stock |
| Carnitine | 197.66 | 2 mM | 4 ml of 500 mM stock |

-continued

| | MW | Final Concentration | Prepare 1 L |
|---|---|---|---|
| Taurine | 125.15 | 5 mM | 20 ml of 250 mM stock |
| Insulin | 5800 | 2.5 µM | 100 µl of 25 mM stock |
| BSA | N/A | 0.2% | 6.6 ml of 30% stock |
| L-glutamine | | 1 mM | 10 ml (see recipe) |
| β-ME | | 0.1 mM | In L-glutamine stock |

Note:
pH to 7.4 with NaOH

Creatine stock solution: Sigma Cat. 27890-100G
Prepare 50 mM of creatine in 100 ml DMEM-Glucose-Pyruvate
Add 0.656 g creatine into 90 ml DMEM-Glucose-Pyruvate and add more to 100 ml
Carnitine stock solution: Sigma Cat. C0283-25G
Prepare 500 mM of carnitine in 25 ml DMEM-Glucose-Pyruvate Add 2.471 g creatine into 20 ml DMEM-Glucose-Pyruvate and add more to 25 ml
Taurine stock solution: Sigma Cat. T8691-100G
Prepare 250 mM of taurine in 50 ml DMEM-Glucose-Pyruvate
Add 1.564 g creatine into 45 ml DMEM-Glucose-Pyruvate and add more to 50 ml
Insulin stock solution: Sigma Cat. I9278-5ML, 10 mg/ml (or 25 mM) stock solution; Ready to use
BSA stock solution: Sigma Cat. A9576-50 ml, 30% in DPBS; Ready to use
DMEM-Glucose-Pyruvate: Invitrogen Cat. 11966-024
L-glutamine stock solution: prepare on a per-use basis
0.146 g L-glutamine—Invitrogen 21051
10 ml Ca/Mg free PBS—Invitrogen 14190
7 µl β-mercaptoethanol—Sigma M7522
The SFGF medium was originally designed by the inventors for use by a third party who had requested media with little or no glucose, and containing galactose as an energy source. The inventors prepared such a media using other design aspects described herein, and surprisingly discovered the ability of such media to maintain the cellular homogeneity of cardiomyocytes, as well as other desirable attributes described herein iCell Cardiac Maintenance Medium (iCMM) is also known as DS-CMM (Dialyzed Serum Cardiac Maintenance Medium). DS-CMM has the same formulation as CMM, except DMEM without glucose or sodium pyruvate is the base medium utilized and dialyzed serum, galactose and sodium pyruvate are added.

DS-CMM is a low glucose containing medium designed to maintain the purity of cardiomyocyte cultures. This is necessary due to the purification process, and the fact that cardiomyocytes do not divide or multiply in culture, whereas the contaminating cells do.

This serum containing medium is designed to maintain the survival of cardiomyocyte cells grown in vitro. The medium has also been designed to maintain the purity cardiomyocyte cells grown in vitro. Culture medium with standard levels of glucose and normal serum induce outgrowth of the non-cardiomyocyte population. This medium maintains the cardiomyocyte purity of the culture for at least 2 weeks.

The medium (DS-CMM) contains:
90% DMEM (No Glucose) Invitrogen—11966-025
10% Dialyzed Fetal Bovine Serum—Millipore SH30079

10 mM Galactose—Sigma G5388
1 mM Sodium Pyruvate—Sigma P4562

DS-CMM (iCMM) Media Preparation:

|  | MW | Final Concentration | Prepare 1 L |
|---|---|---|---|
| DMEM - Glucose - Pyruvate | N/A |  | 870 mL |
| Galactose | 180.16 | 10 mM | 20 mL of 500 mM stock |
| Na Pyruvate | 110.04 | 1 mM | 10 mL of 100 mM stock |
| Dialyzed Serum | NA | 10% | 100 mL |

DMEM-Glucose-Pyruvate: Invitrogen Cat. 11966-025

Galactose Stock Solution: 500 mM solution. Weigh out 4.5 g Galactose, Volume up to 50 mL DMEM-Glucose-Pyruvate.

Na Pyruvate Stock Solution: 100 mM Solution. Weigh out 550 mg, volume up to 50 mL DMEM-Glucose-Pyruvate.

Dialyzed Serum: HyClone SH30079

As a control, CMM (Cardiac Maintenance Medium) could be used. This CMM medium is used during the differentiation process, and was used as the default (control) media for plating experiments for post cryopreserved cells. This medium includes DMEM (Gibco 10567) and fetal bovine serum (Hyclone SH30396).

Metrics and Definitions for the Examples

"Seeding density" refers to the number of cardiomyocytes added to a culture vessel. Calculated by cell counts and purity.

"Plating density" refers to the number of cardiomyocytes attached to culture vessel after 48 hours. Calculated by cell counts and purity.

"Plating efficiency" refers to the percentage of cardiomyocytes attached to the culture vessel (Plating density divided by seeding density) Calculated by cell counts and purity.

"Purity" refers to the percentage of cardiomyocytes in a given culture condition. This could be measured by quantifying the percentage of RFP positive cells in cardiomyocyte cultures derived from an iPS cell line that expresses RFP driven by a cardiomyocyte-specific promoter or by quantifying the percentage of cardiac troponin T positive cells in cardiomyocyte cultures Example 2

Medium that Maintains Cardiomyocyte Purity iCell cardiomyocytes used in the present examples are a purified population of human induced pluripotent stem (iPS) cell derived cardiomyocytes. The iPS starting material has a genetic modification driven by a cardiomyocyte-specific promoter of the MYH6 (alpha myosin heavy chain) gene to express red fluorescent protein (RFP) and a Blasticidin resistance gene used for purification during the manufacturing process. Since cardiomyocytes do not proliferate in culture, the purity is of great importance. Any non-cardiomyocyte cells present may continue to divide in culture, so that the cardiomyocyte culture purity is constantly dropping with time.

The cells were purified to >95% RFP positive measured by flow cytometry prior to cryopreservation and eventual use. Cells were then thawed, seeded into a culture vessel, and allowed to recover for 48 hours before being considered useable for experimentation.

Cardiac Maintenance Medium (CMM) was used as the default thawing/plating and culture medium for iCell Cardiomyocytes unless specified otherwise. CMM is used during the manufacturing process. CMM is made with 10% Fetal Bovine Serum (FBS) and DMEM culture medium.

Serum Free Glucose Free Medium (SFGF) Maintains Cardiomyocyte Purity In Vitro—

When cultured in standard conditions comprising 10% fetal bovine serum and 5.5 mM Glucose, highly purified (>99%) cardiomyocytes will quickly lose purity due to the outgrowth of contaminating cells. In comparison, media prepared without glucose or serum supports equivalent cardiomyocyte survival (FIG. 1A) while inhibiting the outgrowth of contaminating cells, effectively maintaining the culture purity (FIG. 1B).

DS-CMM Medium (iCMM) Maintains Cardiomyocyte Purity In Vitro—

Figures 2A, 2B:
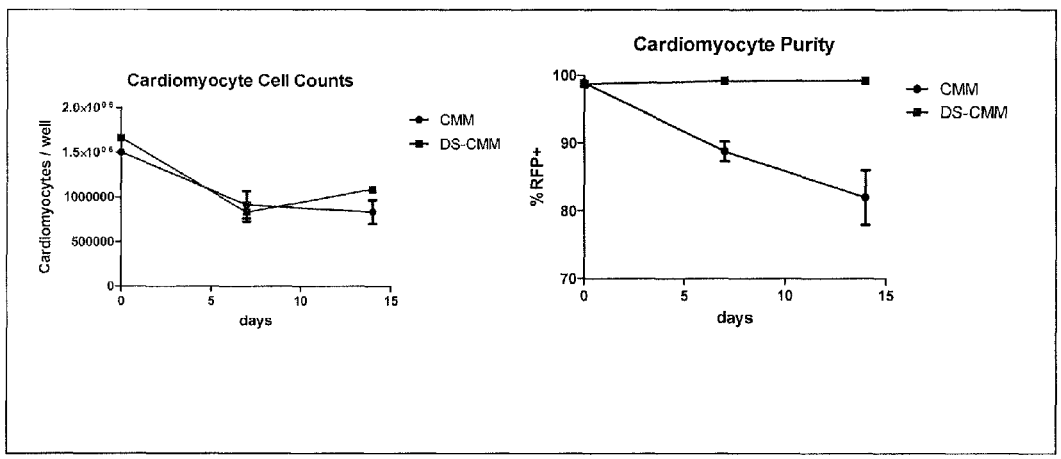
FIGS. 2A-2C: DS-CMM medium maintains cardiomyocyte purity in vitro.
Figure 2C:
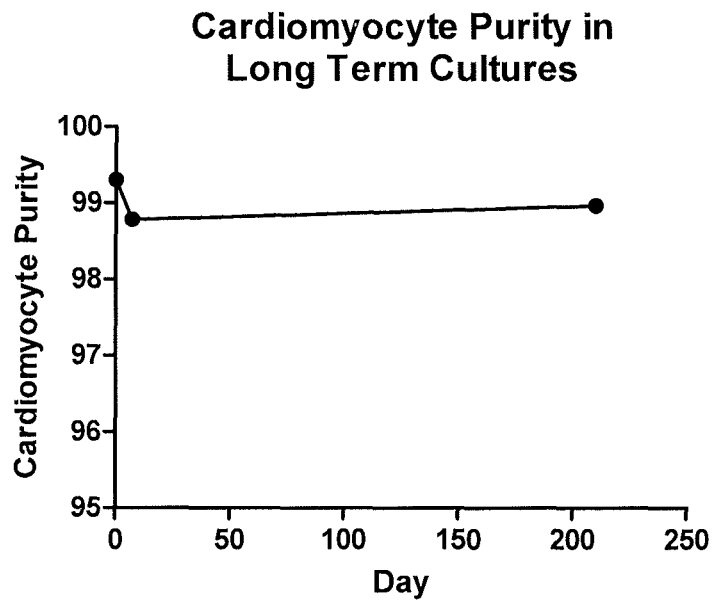

Some of the intended uses for cardiomyocytes may require that serum be present, but that the cardiomyocyte purity also be maintained. Here it is shown that a glucose free DMEM medium comprised of 10% dialyzed serum (10,000 MW cutoff), supplemented with galactose and sodium pyruvate (DS-CMM) maintains equivalent cardiomyocyte survival to control conditions (CMM) (FIG. 2A). The DS-CMM medium also inhibits the outgrowth of contaminating cells, maintaining a culture with high cardiomyocyte purity (FIG. 2B). DS-CMM maintains the purity of cardiomyocytes in culture for extended periods of time. Cardiomyocytes have been cultured in DS-CMM for up to 7 months (210 days) with little or no loss of purity as measured by cardiac troponin T flow cytometry (FIG. 2C).

iCMM Vs. SFGF Vs. CMM—

Figure 3:
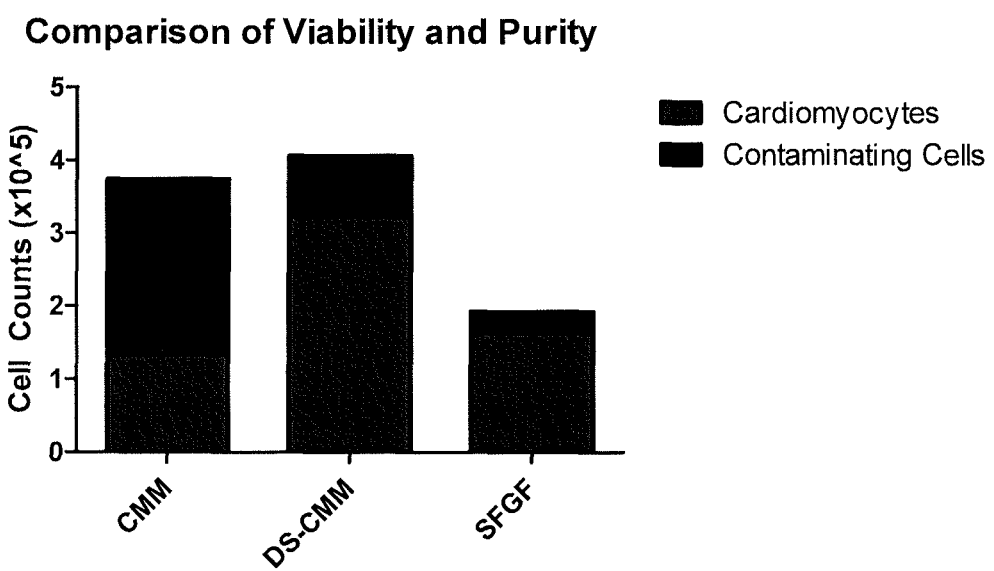
FIG. 3. iCMM vs. SFGF vs. CMM. Cells were seeded into CMM and transitioned to experimental medium at 24 hours. Cell counts and purity was assayed at 7 days. The SFGF medium and iCMM promote higher cardiomyocyte survival and purity after 7 days in culture.

Cells were seeded into CMM and transitioned to experimental medium at 24 hours (FIG. 3). Cell counts and purity was assayed at 7 days. This Experiment shows that the SFGF medium and iCMM promote higher cardiomyocyte survival and purity after 7 days in culture.

Dialyzed Serum Inhibits the Outgrowth of Contaminating Cells—

Figure 4:
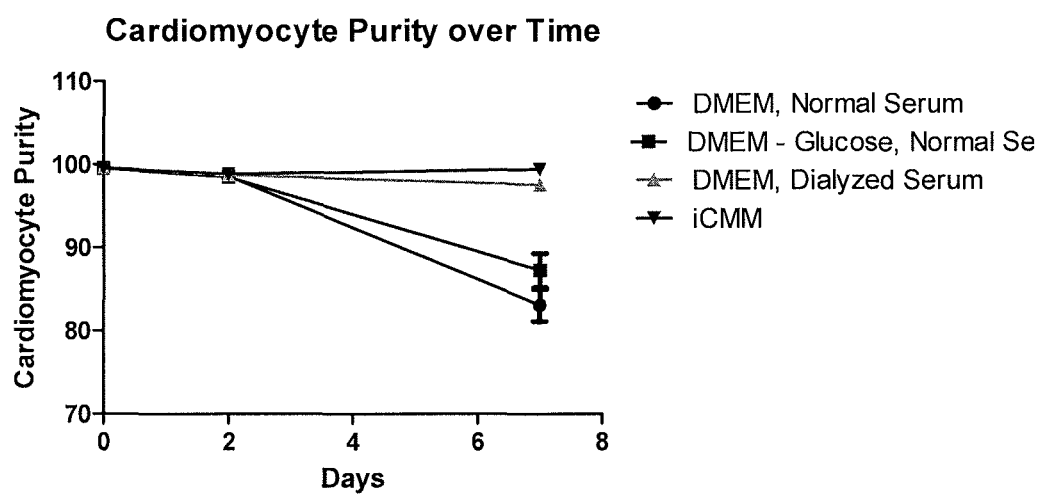
FIG. 4. Dialyzed Serum inhibits the outgrowth of contaminating cells. Cardiomyocytes were cultured in DMEM, Normal Serum; DMEM-Glucose, Normal Serum; DMEM, Dialyzed Serum; or DS-CMM (also called iCMM). The two DMEM conditions prepared with dialyzed serum (DMEM, Dialyzed Serum and DS-CMM) maintained higher cardiomyocyte purity when compared to normal serum containing DMEM medium.

To determine the main component that inhibits the outgrowth of contaminating cells, we examined the role of the dialyzed serum and the role of glucose in the culture medium and found that dialyzed serum inhibits the outgrowth of contaminating cells (FIG. 4). Four media types were prepared with varying glucose concentrations, and either with normal fetal bovine serum or dialyzed fetal bovine serum added. Cardiomyocytes were plated into the four experimental media, and assayed for cardiomyocyte purity after 2 and 7 days. The four media types are as follows: 1. DMEM, Normal Serum (also known as CMM)—5.5 mM Glucose; 2. DMEM-Glucose, Normal Serum—0.55 mM Glucose; 3. DMEM, Dialyzed Serum—4.95 mM Glucose; 4. DMEM-Glucose, Dialyzed Serum (DS-CMM; also known as iCMM)—~0 mM Glucose.

Glucose Concentration Effects Cardiomyocyte Purity to a Lesser Extent—

Figures 5A, 5B:
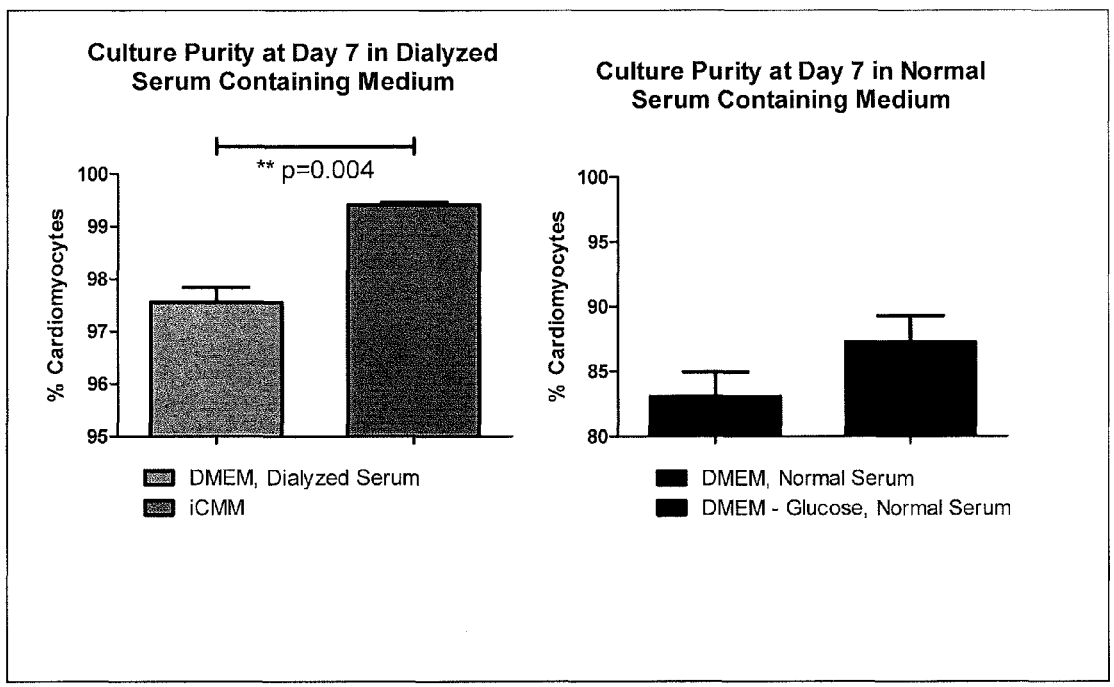
FIGS. 5A-5B: Glucose Concentration effects cardiomyocyte purity to a lesser extent.

When conditions prepared with the same type of serum are compared, the data show that the condition with the lower glucose concentration maintains the higher purity, but the effect of glucose concentration is minimal compared to the effect of the dialyzed serum. When comparing the cardiomyocyte purity of cells cultured in media prepared with DMEM and dialyzed serum (either containing essentially no glucose [iCMM] or 4.95 mM glucose [DMEM-Dialyzed Serum]) the condition essentially lacking glucose (iCMM) maintained significantly higher cardiomyocyte purity (p=0.004) (FIG. 5A). When the treatments made with normal serum and varying levels of glucose were compared, the condition with the lower glucose concentration (DMEM- Glucose, Normal Serum; [Glucose]=0.55 mM) maintains higher cardiomyocyte culture purity than the higher glucose containing medium (DMEM, Normal Serum; [Glucose]=5.5 mM) (FIG. 5B).

Serum Free Glucose Free Medium Produces Faster Beating Monolayers than Serum Containing Media—

Figure 6:
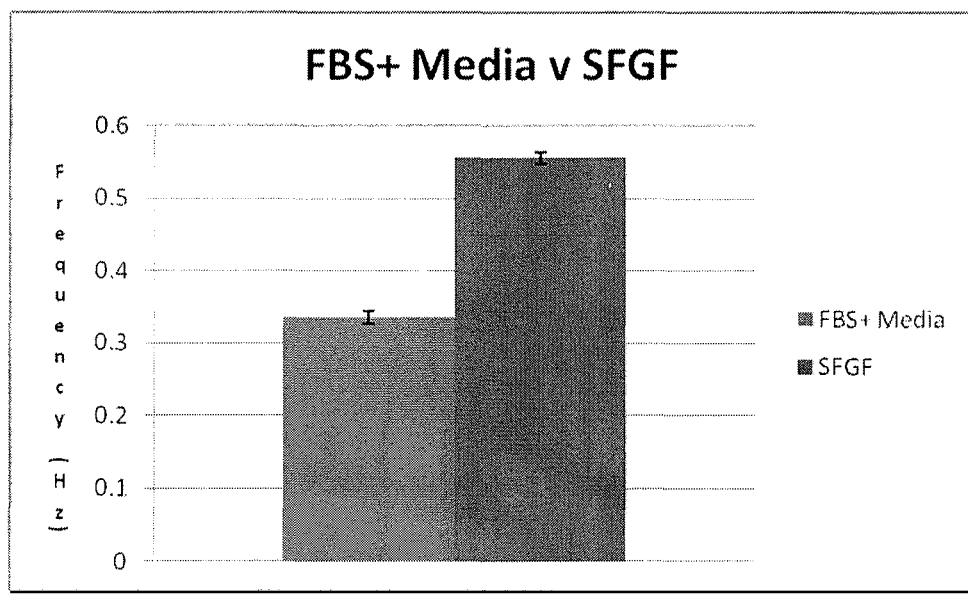
FIG. 6. Serum free glucose free (SFGF) medium produces faster beating monolayers than serum containing media. Cardiomyocyte monolayers cultured in SFGF medium exhibited a more rapid beat rate than monolayers cultured in SFGF medium containing FBS. (N=24 monolayers).

Monolayers cultured in serum free glucose free (SFGF) media beat faster than monolayers cultured in FBS-containing media. Monolayers cultured in FBS containing media beat at an average frequency of 0.34 Hz compared to 0.56 Hz in SFGF (FIG. 6). Cardiomyocytes were pre-plated for three days in tissue culture flasks in either fetal bovine serum-containing medium or in SFGF. These cultures were then trypsinized and plated at 30,000 cells per well on 6-well multi-electrode array (MEA) plates for three days in either fetal bovine serum-containing medium or in SFGF medium. The beat rate (frequency) was measured over a 5 minute period. This data demonstrates that MEA monolayers cultured in SFGF medium beat more rapidly. The increased beating frequency reduces the incidence of beating rate oscillations that can occur in MEA cardiomyocyte beating frequency analysis, thereby increasing the stability of MEA-mediated beating frequency recordings.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,843,780
U.S. Pat. No. 6,200,806
U.S. Pat. No. 6,602,711
U.S. Pat. No. 6,833,269
U.S. Pat. No. 7,029,913
U.S. Appln. 61/058,858
U.S. Appln. 61/172,079
U.S. Appln. 61/184,546
U.S. Publn. 2002/0168766
U.S. Publn. 2003/0022367
U.S. Publn. 20080038820
U.S. Publn. 20080226558
U.S. Publn. 20080254003
U.S. Publn. 20090047739
Amit et al., *Dev. Bio.*, 227:271-278, 2000.
Andrews et al., In: *Teratocarcinomas and Embryonic Stem Cells*, Robertson (Ed.), IRL Press, 207-246, 1987.
Byrne et al., *Nature*, 450(7169):497-502, 2007.
Klimanskaya et al., *Lancet.*, 365(9471):1636-41, 2005.
Marvin et al., *Genes Dev.*, 15(3):316-27, 2001.
Mocellin and Rossi, *Adv. Exp. Med. Biol.* 593:19, 2007.
Pinhasov et al., *Comb. Chem. High Throughput Screen*, 7:133, 2004.
Reubinoff et al., *Nat. Biotechnol.*, 18:399 B404, 2000.
Scalia et al., *J Cell Biochem.*, 82(4):610-8, 2001.
Schneider et al., *Genes Dev.*, 15(3):304-15, 2001.
Smith, In: *Origins and Properties of Mouse Embryonic Stem Cells*, Annu. Rev. Cell. Dev. Biol., 2000.
Takahashi and Yamanaka, *Cell*, 126:663-676, 2006.
Takahashi et al., *Cell*, 126(4):663-76, 2007.
Thomson and Marshall, *Curr. Top. Dev. Biol.*, 38:133-165, 1998.
Thomson and Odorico, *J. Trends. Biotechnol.*, 18:53 B57, 2000.
Thomson et al. *Proc. Natl. Acad. Scie. USA*, 92:7844-7848, 1995.
PCT Appln. WO 01/51616
PCT Appln. WO 03/004626
Xu et al., *Nat. Biotechnol.*, 19:971-974, 2001.
Ying et al., *Cell*, 115:281-292, 2003.
Yu and Thompson, *Genes Dev.*, 22(15):1987-97, 2008.
Yu et al., *Science*, 318:1917-1920, 2007.
Yu et al., *Antimicrob. Agents Chemo.*, 53(10):4311-4319, 2009.
Zhang et al., *Circ Res.*, 104(4):e30-41, 2009.

What is claimed is:

1. A composition comprising a cell population of at least 90% cardiomyocytes and a medium that is essentially free of glucose, wherein said cardiomyocytes are prepared from human induced pluripotent stem (iPS) cells and further wherein said cells have been cultured in said medium for at least 7 days.

2. The composition of claim 1, wherein the medium comprises dialyzed serum.

3. The composition of claim 2, wherein the medium comprises dialyzed serum in a range of about 1% to about 75%.

4. The composition of claim 3, wherein the medium comprises dialyzed serum of at least 10%.

5. The composition of claim 4, wherein the medium comprises dialyzed serum of at least 25%.

6. The composition of claim 4, wherein the medium comprises dialyzed serum of about 55%.

7. The composition of claim 2, wherein said serum has been treated to remove low molecular weight molecules having a molecular weight of at most 10 kD.

8. The composition of claim 2, wherein said serum is essentially free of low molecular weight molecules having a molecular weight of at most 10 kD.

9. The composition of claim 1, wherein the medium does not comprise glucose.

10. The composition of claim 1, wherein the medium comprises about 1 to 20 mM galactose.

11. The composition of claim 1, wherein the medium comprises about 0.1 to 10 mM pyruvate or pyruvic acid.

12. The composition of claim 1, wherein the composition comprises a cell population of at least 95% cardiomyocytes.

13. The composition of claim 1, wherein the cardiomyocytes express at least one selectable or screenable transgene under the control of a cardiomyocyte-specific promoter.

14. The composition of claim 1, wherein the population is essentially free of fibroblasts or undifferentiated pluripotent stem cells.

15. The composition of claim 1, wherein the cardiomyocytes are cryopreserved cardiomyocytes.

* * * * *